(12) United States Patent
Ely et al.

(10) Patent No.: US 8,167,908 B2
(45) Date of Patent: May 1, 2012

(54) POLYAXIAL TRANSVERSE CONNECTOR

(75) Inventors: Kameron Scott Ely, Cedar Park, TX (US); Bruce A. Riceman, Leander, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 720 days.

(21) Appl. No.: 12/201,713

(22) Filed: Aug. 29, 2008

(65) Prior Publication Data

US 2010/0057131 A1  Mar. 4, 2010

(51) Int. Cl.
*A61B 17/70* (2006.01)
(52) U.S. Cl. .................. 606/250; 606/251; 606/253
(58) Field of Classification Search .......... 606/60, 606/61, 72, 73, 246–279
See application file for complete search history.

(56) References Cited

U.S. PATENT DOCUMENTS

| | | | |
|---|---|---|---|
| 6,562,040 B1 | 5/2003 | Wagner | |
| 6,595,992 B1 | 7/2003 | Wagner et al. | |
| 7,090,674 B2 | 8/2006 | Doubler et al. | |
| 7,122,036 B2 * | 10/2006 | Vanacker | 606/250 |
| 7,794,478 B2 * | 9/2010 | Nilsson | 606/251 |
| 2002/0169448 A1 * | 11/2002 | Vanacker | 606/61 |
| 2003/0114853 A1 * | 6/2003 | Burgess et al. | 606/61 |
| 2006/0241602 A1 * | 10/2006 | Jackson | 606/61 |
| 2007/0083201 A1 * | 4/2007 | Jones et al. | 606/61 |
| 2007/0118123 A1 | 5/2007 | Strausbaugh et al. | |
| 2008/0015588 A1 | 1/2008 | Hawkes | |
| 2008/0103507 A1 | 5/2008 | Purcell | |
| 2008/0172093 A1 * | 7/2008 | Nilsson | 606/250 |

\* cited by examiner

*Primary Examiner* — Eduardo C Robert
*Assistant Examiner* — Stuart S Bray
(74) *Attorney, Agent, or Firm* — Seager Tufte Wickhem LLC

(57) ABSTRACT

A polyaxial transverse connector for stabilizing a portion of the spine. Connector bodies are coupled to rods attached to either side of the spine. Heads of transverse members are positioned in the connector bodies such that they exhibit polyaxial motion. The transverse members may have curves or offsets to accommodate other components or patient anatomy. A connector connects the transverse members and male threaded inserts are advanced into the connector bodies to inhibit motion of the polyaxial transverse connector.

13 Claims, 8 Drawing Sheets

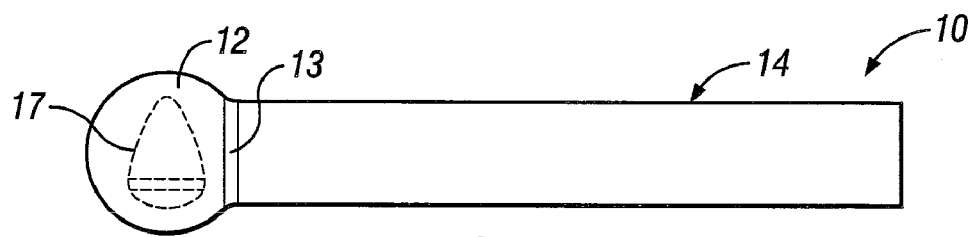
FIG. 2A
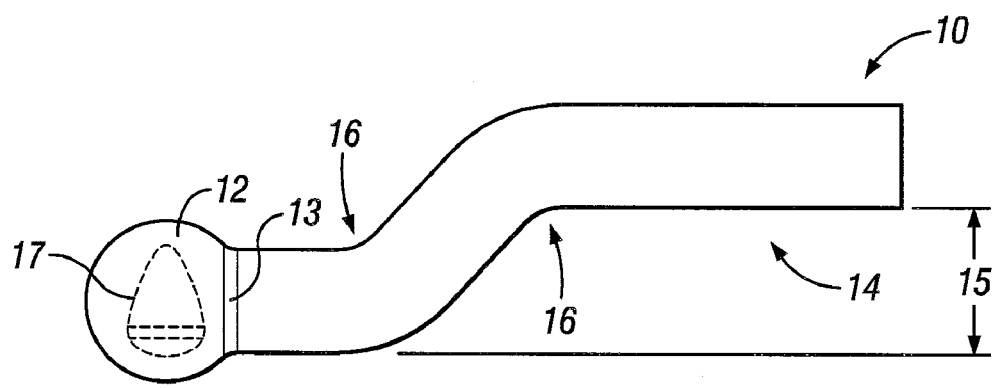
FIG. 2B
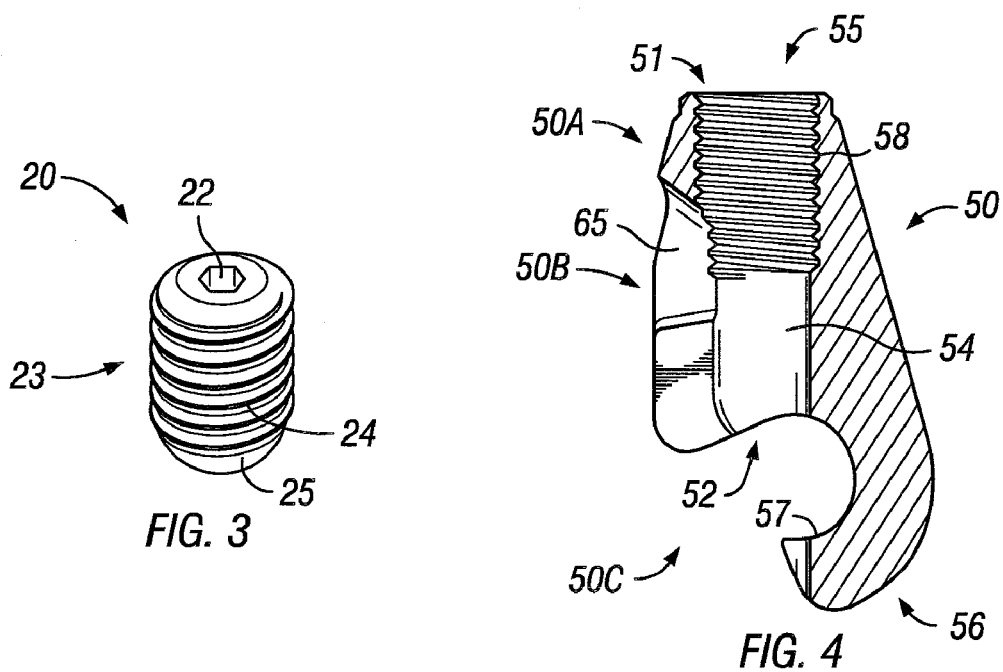
FIG. 3
FIG. 4

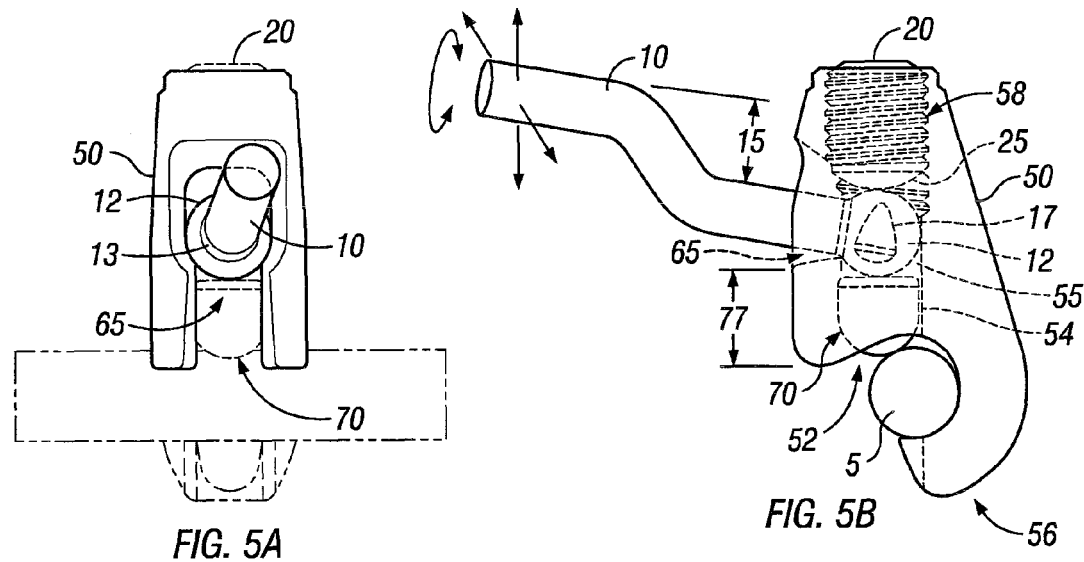
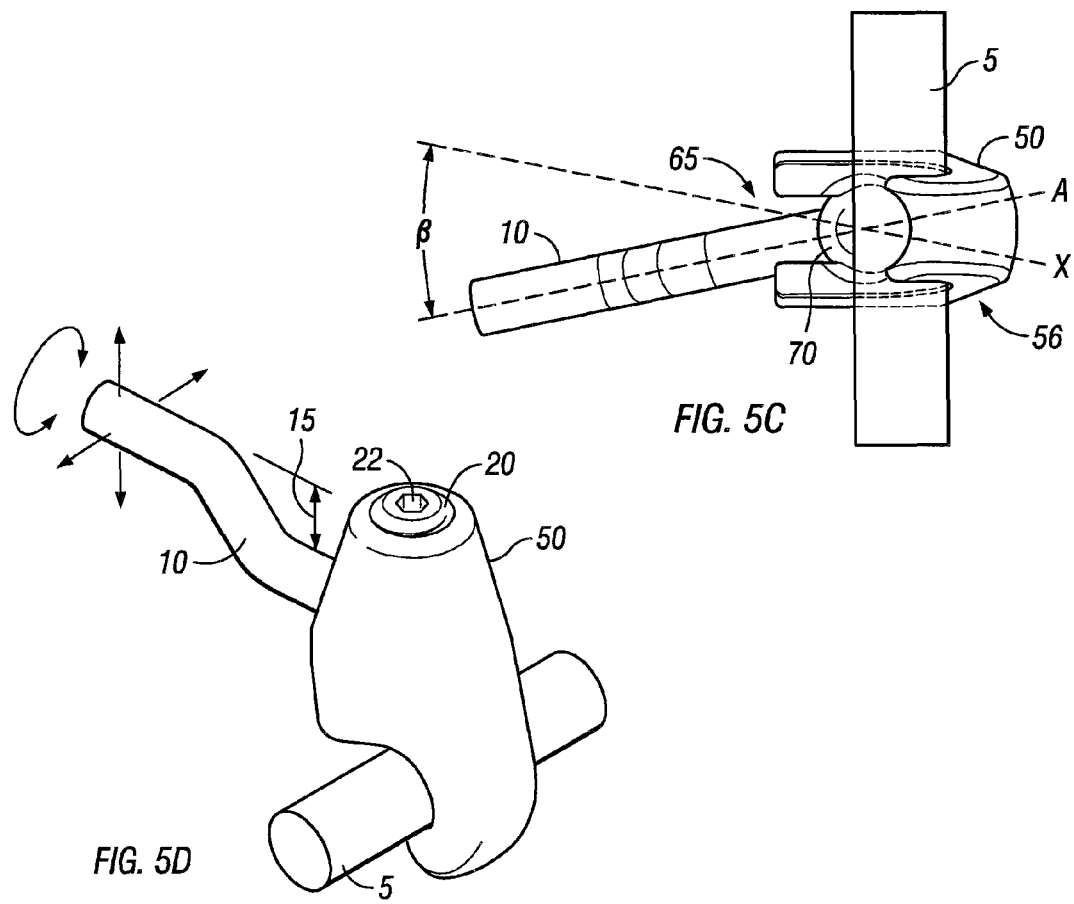
FIG. 5A
FIG. 5B
FIG. 5C
FIG. 5D

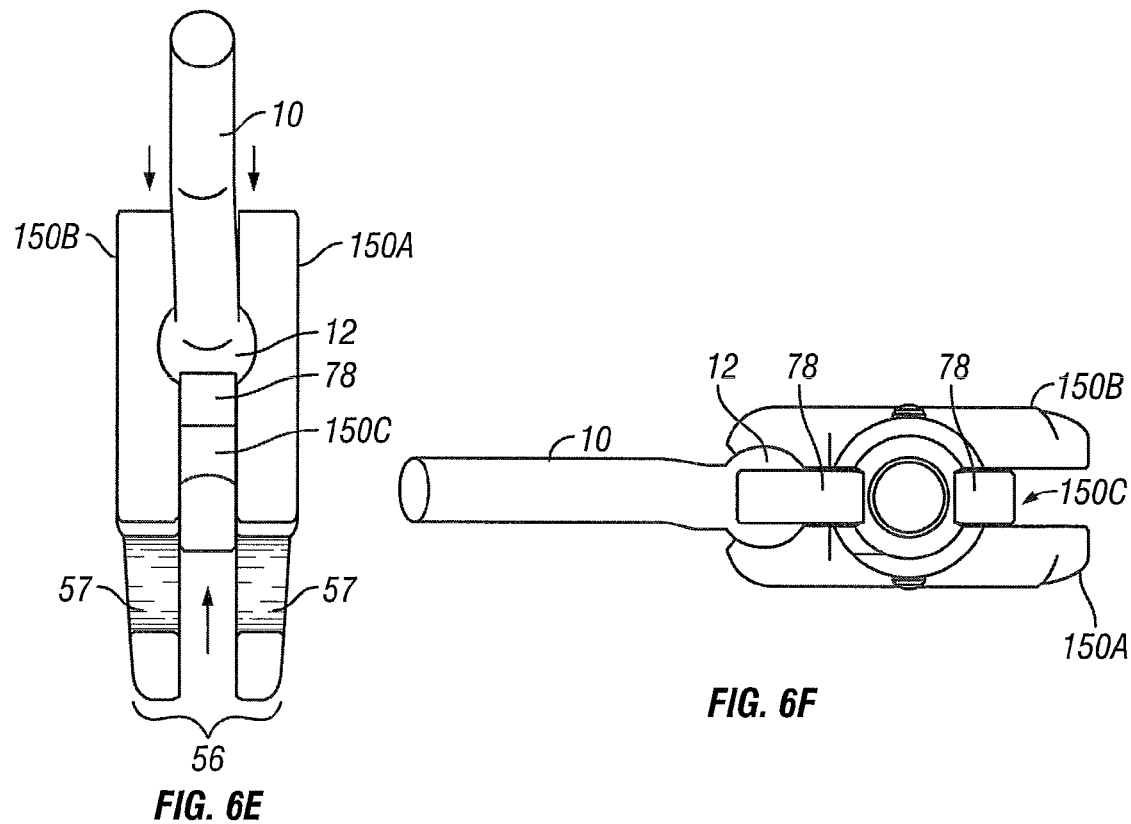
FIG. 6E
FIG. 6F
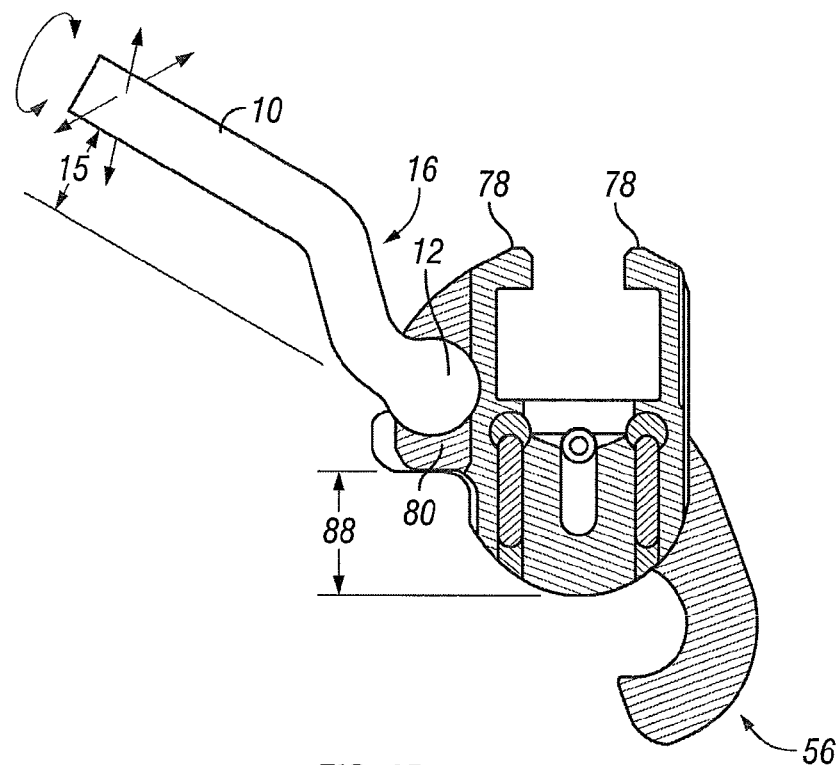
FIG. 6D

POLYAXIAL TRANSVERSE CONNECTOR

TECHNICAL FIELD OF THE DISCLOSURE

The present disclosure generally relates to spinal stabilization systems and in particular to spine stabilization systems in which a polyaxial transverse connector may be implanted in a patient to stabilize spinal rods.

BACKGROUND OF THE DISCLOSURE

The human spine consists of segments known as vertebrae linked by intervertebral disks and held together by ligaments. There are 24 movable vertebrae—7 cervical (neck) vertebrae, 12 thoracic (chest) vertebrae, and 5 lumbar (back) vertebrae. Each vertebra has a somewhat cylindrical bony body (centrum), a number of winglike projections (processes), and a bony arch. The arches are positioned so that the space they enclose forms the vertebral canal. The vertebral canal houses and protects the spinal cord, and within it the spinal fluid circulates. Ligaments and muscles are attached to various projections of the vertebrae. The bodies of the vertebrae form the supporting column of the skeleton. Fused vertebra make up the sacrum and coccyx, the very bottom of the vertebral column.

The spine is subject to abnormal curvature, injury, infections, tumor formation, arthritic disorders, and puncture or slippage of the cartilage disks. Modem spine surgery often involves the use of spinal stabilization/fixation procedures such as a vertebral body fusion procedure to correct or treat various acute or chronic spine disorders and/or to support the spine. In conjunction with these procedures, some spinal implants may be utilized to help stabilize the spine, correct deformities of the spine such as spondylolisthesis or pseudarthrosis, facilitate fusion, or treat spinal fractures. Some spinal implants such as a spinal fixation system may provide fused and/or rigid support for the affected regions of the spine. For example, a spinal fixation system may include a corrective spinal implant that is attached to selected vertebrae of the spine by screws, hooks, and clamps. The corrective spinal implant may include spinal rods or plates that are generally parallel to the patient's back. The corrective spinal implant may also include transverse connecting rods that extend between neighboring spinal rods. Spinal fixation systems can be used to correct problems in the cervical, thoracic, and lumbar portions of the spine, and are often installed posterior to the spine on opposite sides of the spinous process and adjacent to the transverse process. Spinal fixation systems when implanted inhibit movement in the affected regions in virtually all directions.

More recently, so called "dynamic" systems have been introduced. Dynamic spinal stabilization systems can better match a patient's anatomy than some spinal stabilization systems used to provide static support. When implanted in a patient, a dynamic spinal stabilization system can allow at least some movement (e.g., flexion, extension, lateral bending, or torsional rotation) of the affected regions of the spine in at least some of the directions, giving the patient a greater range of motion. Dynamic stabilization systems can be used in scenarios in which vertebral body fusion is not desired, in which vertebral body (re)alignment is desired, and in which it is desired to support or strengthen degraded, diseased, damaged, or otherwise weakened portions of the spine.

Often, spinal stabilization systems include rods which can bear a portion of the forces that would otherwise be transmitted along the spine. These rods may be implanted in pairs or in other numbers along portions of the spine of interest. Some spinal stabilization systems may support a portion of the spine including only two vertebrae (and associated anatomical structures) while some spinal stabilization systems support portions of the spine extending beyond two vertebrae. Spinal stabilizations systems can be used to support various portions of the spine, including the lumbar portion of the spine and the thoracic portion of the spine. Regardless of the number of rods implanted, or the portion of the spine in which they may be implanted, the rods can be attached to one or more vertebrae of the spine to provide support and stabilize, align, or otherwise treat the region of the spine of interest. Surgical personnel may use one or more anchor systems to attach the rods to one or more vertebrae. One such anchor system includes pedicle screws constructs which define slots, keyways, grooves, apertures, or other features for accepting and retaining stabilization rods which may be static, dynamic, or a combination of both. In many pedicle screw constructs, pedicle screws are placed in vertebrae selected by surgical personnel.

SUMMARY OF THE DISCLOSURE

In some embodiments, a polyaxial transverse connector may include a first connector body coupled to a second connector body. The first connector body may be coupled to a first rod. The second connector body may be coupled to a second rod. The first connector body may have a passage formed along an axis of the first connector body. In some embodiments, a head of a first transverse member may be inserted into the passage at a first end. In some embodiments, the head may pass through an opening at a second end of the passage. In some embodiments, the head of the first transverse member can be advanced some distance through the passage. The head of the transverse member may be seated in a cavity formed in the passage. In some embodiments, a portion of the head may protrude from the opening in the second end of the first connector body to contact a first rod positioned in a rod hook of the first connector body. In some embodiments, the transverse member may also have an elongated section. The elongated section may be straight or may have an offset.

A male threaded insert may be inserted into the passage at the first end of the first connector body which may have a corresponding female threaded portion. The male threaded insert may be advanced through the female threaded portion. In some embodiments, a tool may be used to advance the male threaded insert through the female threaded portion of the passage. In some embodiments, a tool may rotate the male threaded insert to engage threads in the passage. In some embodiments, rotation of the male threaded insert may advance the male threaded insert into the passage such that one end of the male threaded insert contacts the head of the first transverse member. In some embodiments, advancement of the male threaded insert into the passage may impinge the head of the transverse member against the first spinal rod to inhibit movement of the spinal rod. In some embodiments, the rod may be inhibited from all movement relative to the first connector body. In some embodiments, impinging the head of the transverse member against the rod inhibits motion of the first connector body relative to the rod.

The transverse polyaxial connector may include a second transverse member having a head and an elongated section. The second connector body may have a passage formed along an axis of the second connector body. In some embodiments, the head of the second transverse member may be inserted into the passage at a first end. In some embodiments, the head may pass through an opening formed in a second end of the passage. In some embodiments, the head of the second transverse member may be advanced some distance through the passage. The head may be positioned in a cavity formed in the passage. In some embodiments, a portion of the head may contact a second rod positioned in the rod hook of the second connector body. A male threaded insert may be inserted into the passage at the first end of the second connector body. The first end may include a female threaded portion. The male threaded insert may be advanced through the female threaded portion. In some embodiments, a tool may be used to advance the male threaded insert through the female threaded portion of the passage. In some embodiments, a tool may rotate the male threaded insert to engage threads in the passage. In some embodiments, rotation of the male threaded insert may advance the male threaded insert into the passage such that an end of the male threaded insert contacts the head of the second transverse member. In some embodiments, continued advancement of the male threaded insert into the passage impinges the head of the transverse member against the first spinal rod to inhibit movement of the spinal rod. In some embodiments, the rod may be inhibited from all movement relative to the second connector body. In some embodiments, impinging the head of the transverse member against the rod inhibits motion of the second connector body relative to the rod.

In some embodiments, a method for stabilizing a portion of a spine may include affixing two rods to the spine such that a first spinal rod is positioned on a first side of the spine and a second spinal rod is positioned on a second side of the spine contralateral to the first rod. A first connector body of a polyaxial transverse connector may be advanced into the patient and positioned on the first rod. In some embodiments, the first connector body may have a rod hook extending therefrom. The first rod may be positionable in the rod hook. A first transverse member of the polyaxial transverse connector may be advanced into the patient. In some embodiments, the head of the first transverse member may be advanced into a passage in a first end of the first connector body. In some embodiments, the passage may have a cavity formed in a portion thereof for seating the head of the first transverse member. The passage may open into a second end of the first connector body. The head of the first transverse member may be seated in the cavity such that a portion of the head protrudes from the opening in the second end of the first connector body. In some embodiments, a plunger or other intermediary device may be advanced into the passage. In some embodiments, the plunger may be positioned in the cavity such that a portion of the plunger extends from the opening in the second end of the first connector body. In some embodiments, the plunger or the head of the first transverse member may contact the first rod positioned in the first rod hook.

In some embodiments, the head of the first transverse member may define a pivot for an axis of rotation. The first transverse member may have a first range of motion when the head is positioned in the passage. In some embodiments, the first transverse member may have a first range of motion when the head is positioned in the cavity. In some embodiments, the first range of motion may allow 360 degree rotation around an axis of rotation.

In some embodiments, a male threaded insert may be advanced into the patient. The male threaded insert may be advanced into the female threaded portion of the passage. In some embodiments, advancement of the male threaded insert into the female threaded portion of the passage causes an end of the male threaded insert to contact the head of the first transverse member or the plunger. In some embodiments, advancement of the male threaded insert into the passage advances the head of the first transverse member or plunger to impinge the first rod between the plunger or head of the first transverse member and a portion of the rod hook. In some embodiments, advancement of the male threaded insert to impinge the first rod impinges the head of the first transverse member, which impinges the head of the first transverse member between the male threaded insert and the rod or the plunger. In some embodiments, impingement of the head of the first transverse member inhibits motion of the first transverse member relative to the first connector body.

A second connector body may be advanced into the patient and positioned on the second rod. In some embodiments, the second connector body may have a rod hook extending therefrom. The second rod may be positionable in the rod hook. A second transverse member may be advanced into the patient. In some embodiments, the head of the second transverse member may be advanced into a passage in a first end of the second connector body. In some embodiments, the passage may have a cavity formed in a portion thereof for seating the head of the second transverse member. The passage may open into a second end of the second connector body. The head of the second transverse member may be seated in the cavity such that a portion of the head protrudes from the opening in the second end of the second connector body. In some embodiments, a plunger or other intermediary device may be advanced into the passage. In some embodiments, the plunger may be positioned in the cavity such that a portion of the plunger extends from the opening in the second end of the second connector body. In some embodiments, the plunger or the head of the second transverse member may contact the second rod positioned in the rod hook.

In some embodiments, the head of the second transverse member may define a pivot for an axis of rotation. The second transverse member may have a first range of motion when the head is positioned in the passage. In some embodiments, the second transverse member may have a first range of motion when the head is positioned in the cavity. In some embodiments, the first range of motion may allow 360 degree rotation around an axis of rotation. Embodiments may provide three degrees of freedom for rotating a transverse member about the head of the transverse member.

In some embodiments, a male threaded insert may be advanced into the patient. The male threaded insert may be advanced into the female threaded portion of the passage. In some embodiments, advancement of the male threaded insert into the female threaded portion of the passage causes an end of the male threaded insert to contact the head of the second transverse member or the plunger. In some embodiments, advancement of the male threaded insert into the passage advances the head of the second transverse member or plunger to impinge the second rod between the plunger or head of the second transverse member and a portion of the rod hook. In some embodiments, advancement of the male threaded insert to impinge the second rod impinges the head of the second transverse member, which impinges the head of the second transverse member between the male threaded insert and the rod or the plunger. In some embodiments, impingement of the head of the second transverse member inhibits motion of the second transverse member relative to the second connector body.

In some embodiments, an elongated portion of the first transverse member and an elongated portion of the second transverse member may be connected. In some embodiments, the elongated portion of the first transverse member and the elongated portion of the second transverse member may be coupled between the first rod and the second rod. A connector having a first opening and a second opening may be advanced into the patient and positioned between the first rod and the second rod. The elongated portion of the first transverse member may be inserted into the first opening and the elongated portion of the second transverse member may be inserted into the second opening. In some embodiments, the elongated portion of the second transverse member may be aligned near the elongated portion of the first transverse member. In some embodiments, a set screw may impinge the elongated portion of the first transverse member inside the connector. In some embodiments, a set screw may impinge the elongated portion of the second transverse member inside the connector. In some embodiments, the connector may impinge the elongated portion of the first transverse member against the elongated portion of the second transverse member.

In one embodiment, a method for inserting a stabilization system in a spine may involve determining one or more vertebrae of the spine to be targeted for stabilization, making an incision in the skin, inserting a spinal stabilization system, and closing the incision in the skin.

Other objects and advantages of the embodiments disclosed herein will be better appreciated and understood when considered in conjunction with the following description and the accompanying drawings.

BRIEF DESCRIPTION OF THE DRAWINGS

A more complete understanding of the present disclosure and the advantages thereof may be acquired by referring to the following description, taken in conjunction with the accompanying drawings in which like reference numbers indicate like features and wherein:

FIG. 2A depicts a side view of one embodiment of a transverse member;

FIG. 2B depicts a side view of one embodiment of a transverse member;

FIG. 3 depicts a perspective view of one embodiment of a male threaded insert;

FIG. 4 depicts a cross-sectional view of one embodiment of a connector body;

FIGS. 5A-5D depict views of a portion of one embodiment of a polyaxial transverse connector;

FIGS. 6D-6F depict views of portions of one embodiment of a polyaxial transverse connector.

DETAILED DESCRIPTION

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

Figure 1:
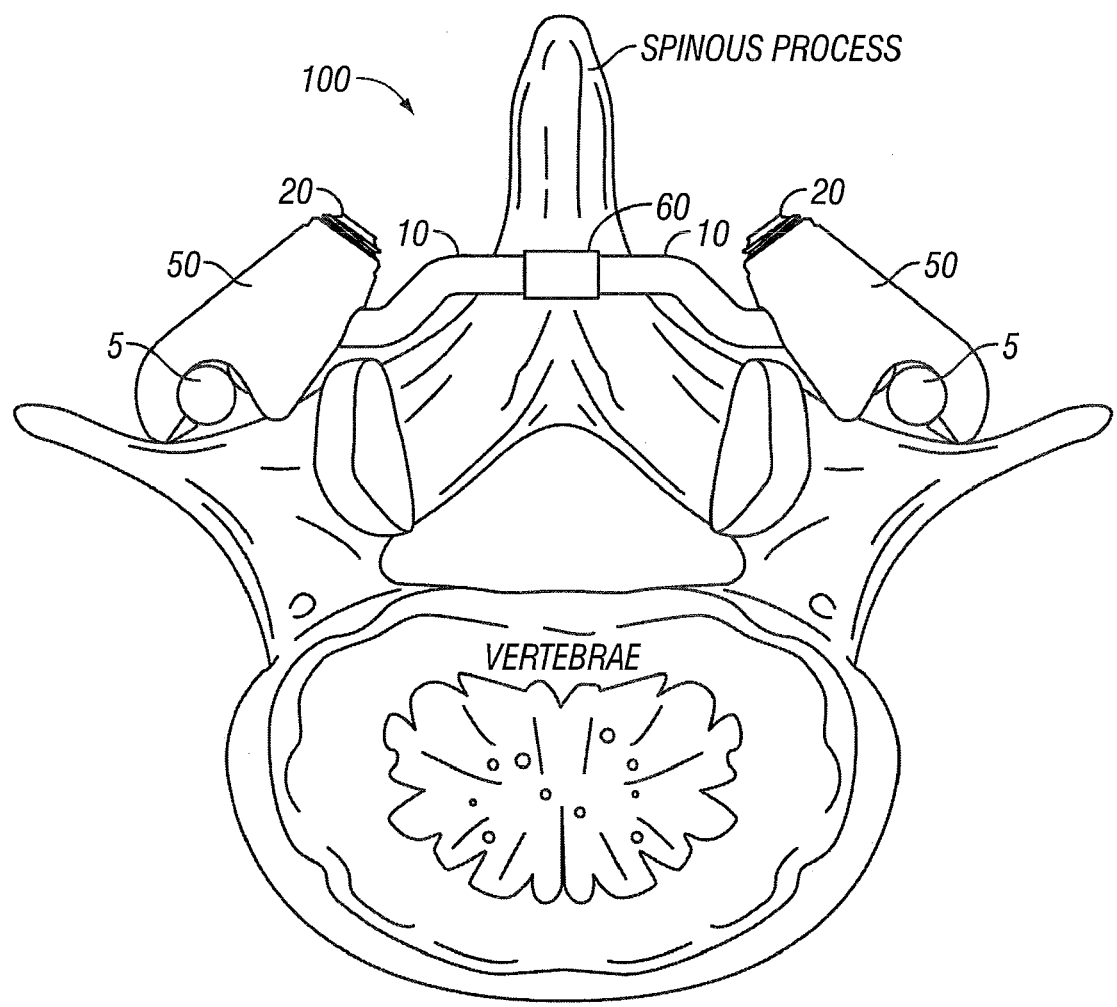
FIG. 1 depicts a perspective view of one embodiment of a spine stabilization system.

FIG. 1 depicts a perspective view of spine stabilization system 100 coupled to rods 5 positioned on a portion of a spine. In some embodiments, bone fasteners (not shown) may be used to couple rods 5 to two or more vertebrae. The bone fasteners may be advanced into the patient and positioned in the pedicle portion of the vertebrae. A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments. A bone fastener assembly may be stamped with indicia (i.e., printing on a side of the collar). In some embodiments, a bone fastener assembly or a bone fastener may be color-coded to indicate a length of the bone fastener. In certain embodiments, a bone fastener with a 30 mm thread length may have a magenta color, a bone fastener with a 35 mm thread length may have an orange color, and a bone fastener with a 55 mm thread length may have a blue color. Other colors may be used as desired.

Each bone fastener provided in an instrumentation set may have substantially the same thread profile and thread pitch. In an embodiment, the thread may have about a 4 mm major diameter and about a 2.5 mm minor diameter with a cancellous thread profile. In certain embodiments, the minor diameter of the thread may be in a range from about 1.5 mm to about 4 mm or larger. In certain embodiments, the major diameter of the thread may be in a range from about 3.5 mm to about 6.5 mm or larger. Bone fasteners with other thread dimensions and/or thread profiles may also be used. A thread profile of the bone fasteners may allow bone purchase to be maximized when the bone fastener is positioned in vertebral bone.

Rods 5 may be coupled to a plurality of bone fasteners located on either side of the spine. Rods 5 coupled to two or more bone fasteners in the vertebrae may run along a portion of the spine. The position of the bone fasteners in the vertebra may determine the distance or positioning of rods 5 relative to the spine or components of the spine. In one embodiment, rod 5 of desired length may be chosen by estimating a distance between sleeves connected to the bone fasteners without the use of an estimating tool. The sleeves may be positioned as desired (e.g., substantially parallel to each other). A distance between the most distant outer edges of the sleeves may be estimated. The estimated distance may be increased by an amount to allow rod 5 to extend beyond the bone fastener assemblies after insertion. In some embodiments, from about 1 mm to about 20 mm may be added to the estimated distance. In some embodiments, a desired length of rod 5 may be a length that allows rod 5 to extend from each bone fastener by about 2 mm.

Rod 5 may be cut to length and contoured as desired. For example, a medical practitioner may use experience and judgment to determine a curvature of rod 5 for a patient. A desired curvature for rod 5 may be determined using fluoroscopic imaging. In some embodiments, a curvature of rod 5 may be chosen such that, when rod 5 is secured to the bone fastener assemblies, sleeves coupled to the bone fastener assemblies cross at a surface of the skin. Crossing of the sleeves at a surface of the skin allows the medical practitioner to minimize trauma to a patient by minimizing incision length and tissue plane area. Rod 5 may be bent or shaped with a tool (e.g., a rod bender) to allow insertion of rod 5 through channels of sleeves with various spatial locations and/or various angular orientations.

Rods 5 may have shapes including, but not limited to, straight, bent, curved, s-shaped, and z-shaped. In some embodiments, rods 5 may have a substantially circular longitudinal cross section. An instrumentation kit for a spinal stabilization system may include straight rods 5 and/or pre-shaped rods 5. Straight rods 5 and/or pre-shaped rods 5 may be contoured to accommodate patient anatomy if needed during the surgical procedure.

In some embodiments, it may be desirable that rods 5 be positioned close to the dural space of the vertebrae, near the spinous process, or proximate some other anatomical landmark, organ or feature of the body. In some embodiments, spine stabilization system 100 may be coupled to spinal rods 5 to add support or rigidity to a portion of the spine near a spinous process, near the dural space, or the like.

Spine stabilization system 100 may include first connector body 50 coupled to first rod 5, second connector body 50 coupled to second rod 5, first transverse member 10 coupled to first connector body 50, second transverse member 10 coupled to second connector body 50, and connector 60 for connecting first transverse member 10 to second transverse member 10. In some embodiments, first connector body 50 may include male threaded insert 20 for securely coupling rod 5 to first connector body 50. In some embodiments, second connector body 50 may include male threaded insert 20 for securely coupling rod 5 to second connector body 50.

FIGS. 2A and 2B depict views of embodiments of transverse members 10. In some embodiments, transverse member 10 may include head 12 and elongated section 14. In some embodiments, head 12 may have keyed surfaces 17. In some embodiments, keyed surfaces 17 maybe flattened surfaces of an otherwise arcuate head 12. In some embodiments, keyed surfaces 17 may be curved surfaces with a different curvature than other surfaces of arcuate head 12. In some embodiments, transverse member 10 may include neck 13.

In some embodiments, elongated section 14 of transverse member 10 may be substantially straight, such as depicted in FIG. 2A. In some embodiments, elongated section 14 of transverse member 10 may have one or more curves, angles or bends 16, such as depicted in FIG. 2B. In some embodiments, a pair of curves or bends 16 may define offset 15. Offset 15 may be based in terms of distance. As an example, one embodiment may have a 5 mm offset. Offset 15 may also be based in terms of structures, landmarks or organs in the patient that offset 15 is designed to accommodate. For example, offset 15 may have selected bends 16 to allow spine stabilization system 100 to stabilize a portion of the spine without contacting a spinous process on a vertebra. In some embodiments, an instrumentation set may include various transverse members 10 having selected offsets 15. In some embodiments, an instrumentation set may include transverse members 10 having a range of offsets 15.

In some embodiments, elongated section 14 may have a flattened end, a flange, or some other terminus (not shown). In some embodiments, elongated section 14 may include markings or indicia indicating a length of transverse member 10. An instrumentation set may include transverse members 10 having various elongated sections 14. Transverse members 10 in an instrumentation set may include markings, colors, or other indicia of the length of elongated section 14. Transverse members 10 in an instrumentation set may include markings, colors, or other indicia of the number or angle of bends 16 in elongated section 14. Transverse members 10 in an instrumentation set may include markings, colors, or other indicia of the diameter of head 12, shape of keyed surfaces 17, or some other aspect of transverse member 10.

FIG. 3 depicts a perspective view of one embodiment of male threaded insert 20 which may be useful for releasably coupling connector body 50 to rod 5 or head 12. In some embodiments, male threaded insert 20 may be cannulated. In some embodiments, male threaded insert 20 may have a solid central core. Male threaded insert 20 with a solid central core may allow more contact area between male threaded insert 20 and a driver used to couple male threaded insert 20 to connector body 50.

In some embodiments, male threaded insert 20 may include shank 23. Shank 23 may have thread 24 around a portion thereof. In some embodiments, male threaded insert 20 may include tool portions 22. In some embodiments, tool portions 22 may have an interior dimension for accepting a hex driver or other surgical tools. In some embodiments, tool portions 22 may protrude from shank 23 for connection with a wrench, driver or other surgical tools.

End 25 of male threaded insert 20 may include structure and/or texture to facillitate contact between male threaded insert 20 and head 12 of transverse member 10, plunger 70, or some other component of spine stabilization system 100. In some embodiments, rotation of male threaded insert 20 when threads 24 are engaged with mated threads may advance end 25 of male threaded insert 20 into contact with another surface. In some embodiments, end 25 may be arcuate. In some embodiments, end 25 may be convex. In some embodiments, end 25 may be concave. In some embodiments, end 25 may be substantially flat.

FIG. 4 depicts a cross sectional view of one embodiment of connector body 50. In some embodiments, connector body 50 may have first end 50A, middle portion 50B, and second end 50C. The size or length of first end 50A, middle portion 50B and second end 50C may determine the overall height of connector 50. In some embodiments, the overall height of connector 50 may determine an offset attainable by embodiments of spine stabilization system 100.

In some embodiments, first end 50A may include opening 51 with female threaded portion 58 having threads for mated engagement of male threaded insert 20. In some embodiments, passage 55 may include female threaded portion 58. Female threaded portion 58 of connector body 50 may have mated threads for engaging male threaded insert 20. In some embodiments, head 12 of transverse member 10 may be inserted into first end 50A of passage 55, such as depicted in FIG. 5A. Male threaded insert 20 may be inserted into first end 50A of passage 55 and advanced through female threaded portion 58 to advance head 12 into cavity 54.

In some embodiments, middle portion 50B may include a portion of passage 55 and cavity 54. In some embodiments, head 12 of transverse member 10 may be positioned in cavity 54. In some embodiments, head 12 positioned in cavity 54 may exhibit polyaxial movement such that transverse member 10 maybe positioned in a selected orientation relative to connector body 50.

In some embodiments, such as depicted in FIG. 4, cavity 54 and passage 55 may be connected, such that head 12 of transverse member 10 may pass through passage 55 into cavity 54. In some embodiments, cavity 54 may be formed with opening 52, such that head 12 of transverse member 10 may pass through second opening 52 into cavity 54.

In some embodiments, connector body 50 may include rod hook 56. In some embodiments, second end 50C may include rod hook 56. In some embodiments, inner surface 57 of rod hook 56 may have a radius of curvature to accommodate rod 5. In some embodiments, a portion of inner surface 57 may define a radius of curvature such that rod 5 may be seated in rod hook 56 and connector body 50 may rotate freely about rod 5. In some embodiments, a portion of inner surface 57 may define a radius of curvature such that rod 5 may fit in rod hook 56 and connector body 50 may be rotated about rod 5 when sufficient force is applied.

Rod hook 56 may enable connector body 50 to couple to rod 5. In some embodiments, rod hook 56 may have a geometric configuration such that when rod 5 is seated in rod hook 56, rod 5 may be near second opening 52. In some embodiments, rod hook 56 may position rod 5 close to second opening 52 such that, when head 12 is positioned in cavity 54 and a portion of head 12 protrudes through second opening 52, head 12 may contact rod 5.

In some embodiments, head 12 of transverse member 10 may be advanced into passage 55 for positioning in cavity 54. In some embodiments, passage 55 may include first opening 51 at first end 50A of connector body 50 and second opening 52 at second end 50C of connector body 50. In some embodiments, head 12 may be inserted into opening 51 in first end 50A of passage 55 and advanced into cavity 54. In some embodiments, head 21 may be inserted into second opening 52 in second end 50C of passage 55 and advanced into cavity 54.

FIGS. 5A-5D depict views of a portion of one embodiment of a polyaxial transverse connector. FIG. 5A depicts one embodiment of connector body 50 having cutout 65 in a portion thereof. In some embodiments, cutout 65 may provide a larger range of motion of spine stabilization system 100 during installation than connectors without cutouts. In some embodiments, a larger range of motion may enable transverse member 10 to be advanced into a patient such that head 12 is positionable in cavity 54 and then transverse member 10 may be rotated into position. In some embodiments, such as depicted in FIG. 5A, transverse member 10 may be advanced "head first" into passage 55.

In some embodiments, once head 12 is positioned in cavity 54, transverse member 10 may be rotated such that elongated section 14 extends through cutout 65. FIG. 5B depicts a perspective view of the embodiment depicted in FIG. 5A, with elongated section 14 of transverse member 10 extending through cutout 65 when head 12 is positioned in connector body 50. Once head 12 is positioned in cavity 54, transverse member 10 may be rotated about head 12 with three degrees of freedom.

FIG. 5B further depicts a view one embodiment of connector body 50 having plunger 70 positioned between head 12 of transverse member 10 and rod 5. In some embodiments, plunger 70 may provide offset 77 such that a portion of transverse member 10 does not contact nearby nerves, bony structures, or the like. In some embodiments, offset 77 and offset 15 described above can be customized for each patient.

FIG. 5C depicts a view of connector body 50 once head 12 has been positioned in connector body 50 and elongated section 14 has been rotated to extend through cutout 65. In some embodiments, cutout 65 may be configured to provide a selected range of motion such that elongated section 14 may extend out of connector body 50 at a selected angle β (beta). In some embodiments, the angle β (beta) may lie within 15 degrees. In some embodiments, the angle β (beta) may lie within 10 degrees. In some embodiments, the angle β (beta) may lie within 5 degrees.

FIG. 5D depicts a perspective view of connector body 50 connected to transverse member 10 and rod 5. In some embodiments, rod 5 may provide an axis for rotation of connector body 50. In some embodiments, transverse member 10 may be rotated about an axis of passage 55 to provide a selected configuration of spine stabilization system 100. In some embodiments, head 12 positioned in connector body 50 may provide one or more axes of rotation, such as depicted in FIGS. 5B, 5C and 5D. Thus, by rotating one or more of connector body 50 about rod 5, transverse member 10 about an axis of passage 55, and transverse member 10 about head 12, spine stabilization system 100 may be assembled in a desired configuration. Furthermore, by selecting transverse member 10 having elongated section 14 with a desired offset 15 or positioning plunger 70 with a desired offset 77 in connector body 50, embodiments may avoid contact with nerves, bony structures, or the like, may provide support along a desired trajectory or at a selected angle, and other advantages.

In some embodiments, connector body 50 may comprise several components joined together. FIGS. 6A-6F depict views of one embodiment of connector body 50 connected to transverse member 10 and secured with male threaded insert 20.

Figure 6A:
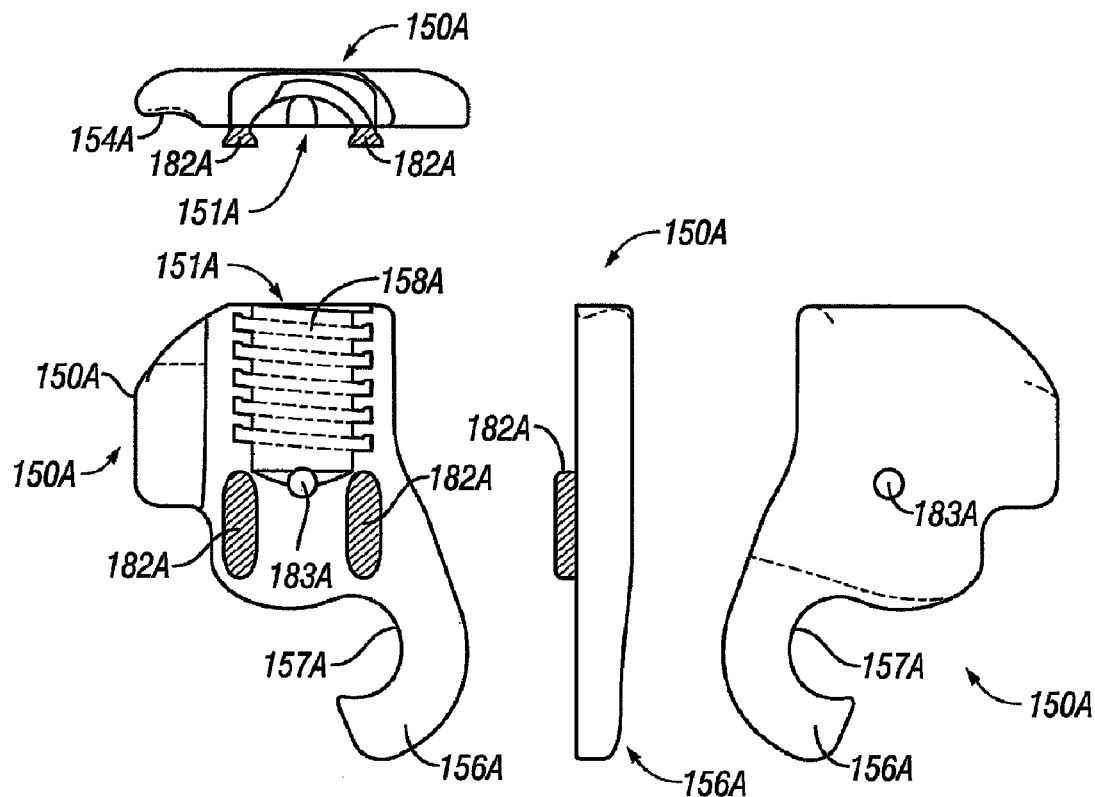
FIG. 6A depicts side and top views of one embodiment of a side plate.
Figure 6B:
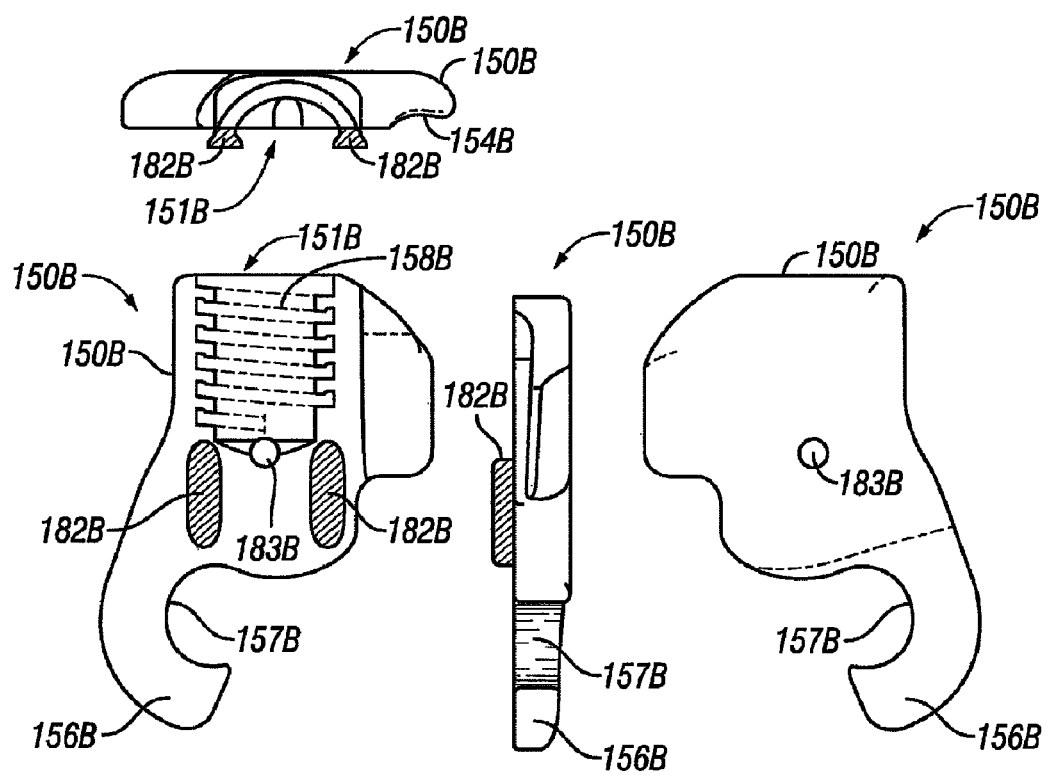
FIG. 6B depicts side and top views of one embodiment of a side plate.
Figure 6C:
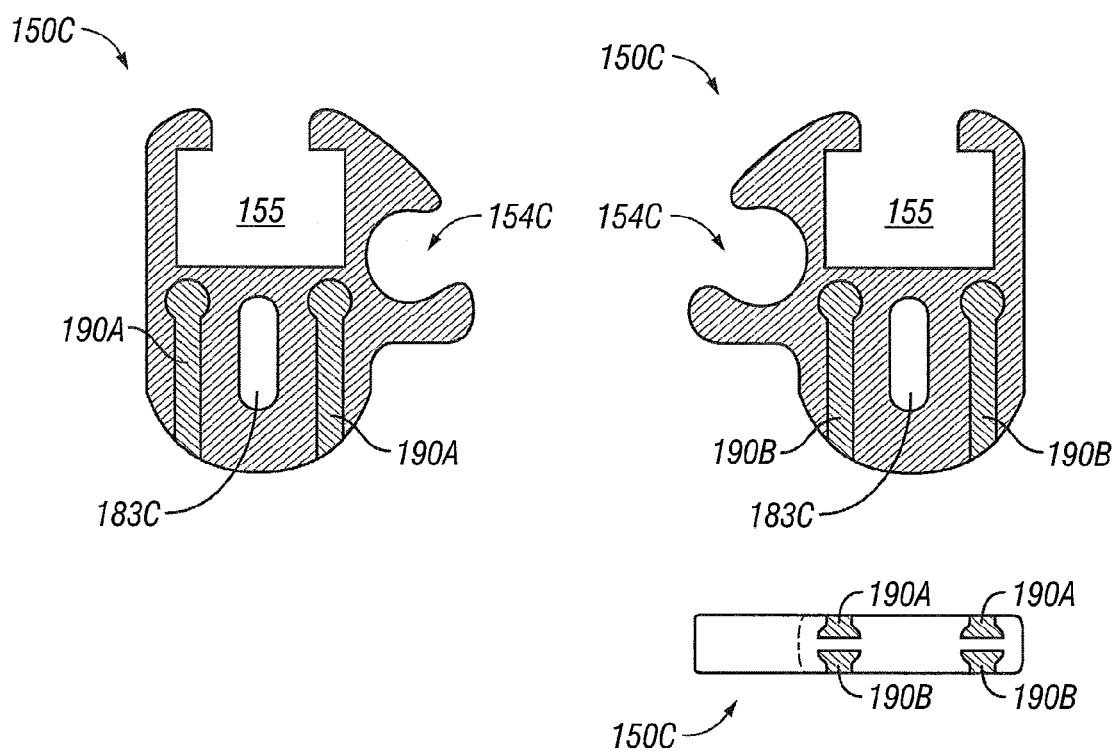
FIG. 6C depicts side and top view of one embodiment of a center plate.

FIGS. 6A-6C depict views of components of connector body 50. In some embodiments, connector body 50 may comprise three plates: two side plates 150A and 150B and center plate 150C. FIG. 6A depicts side and top views of one embodiment of side plate 150A. FIG. 6B depicts side and top views of one embodiment of side plate 150B. FIG. 6C depicts side and top view of one embodiment of center plate 150C.

Side plates 150A and 150B may connect with center plate 150C in various ways. In some embodiments, protrusions 182A and 182B on side plates 150A and 150B may be positioned in slots 190A and 190B of center plate 150C. Sides 150A and 150B may be advanced until protrusions 182A and 182B are at a selected position in slots 190A and 190B. In some embodiments, sides 150A and 150B may be advanced with protrusions 182A and 182B in slots 190A and 190B of center plate 150C until openings 183A and 183B on sides 150A and 150B align with slot 183C in center plate 150C. In some embodiments, a pin may be positioned in opening 183A, opening 183B and slot 183C such that the pin inhibits motion of side 150A relative to 150B but allows motion of center plate 150C relative to both sides 150A and 150B.

In some embodiments, features 154A, 154B and 154C may align to form cavity 54. Head 12 of transverse member 10 may be positioned in cavity 54. When head 12 is positioned in cavity 54, head 12 may exhibit polyaxial motion.

In some embodiments, side plates 150A and 150B have inner surfaces 151A and 151B. In some embodiments, each of sides 150A and 150B may have female threaded portions 158A and 158B on inner surfaces 151A and 151B such that, when assembled, inner surfaces 151A and 151B define female threaded portion 58. In some embodiments, each of sides 150A and 150B may have a recessed portion on inner surfaces 151A and 151B such that, when assembled, inner surfaces 151A and 151B may help define cavity 54 for head 12 of transverse member 10.

In some embodiments, female threaded portions 158A and 158B and opening 155 may be aligned to form passage 55 having female threaded portion 58. In some embodiments, male threaded insert 20 may be inserted in opening 51 formed by opening 151C and inner surfaces 151A and 151B. In some embodiments, male threaded insert 20 maybe advanced and positioned in passage 55 formed by female threaded portions 158A and 158B and opening 155. In some embodiments, when male threaded insert 20 is positioned in passage 55 formed by female threaded portions 158A and 158B and opening 155, rotation of male threaded insert 20 may bias sides 150A and 150B in a first direction and bias center plate 150C in an opposite direction. In some embodiments, biasing side plates 150A and 150B in a first direction while biasing center plate 150C in an opposite direction impinges head 12 positioned in cavity 54 to inhibit polyaxial motion of head 12.

In some embodiments, sides 150A and 150B may include portions 156A and 156B of rod hook 56. In some embodiments, when rod 5 is positioned in rod hook 56 formed by portions 156A and 156B of rod hook 56, biasing side plates 150A and 150B in a first direction while biasing center plate 150C in an opposite direction (depicted by arrows in FIG. 6E) impinges rod 5 between inner surfaces 157A and 157B of rod hook 56 and center plate 150C. Biasing may be accomplished, for example, by protrusions 182A and 182B sliding in slots 190A and 190B.

FIG. 6D-6F depict views of one embodiment of connector body 50 formed with several components. As depicted in FIG. 6D, connector body 50 formed from multiple components may provide offset 15, offset 88, and other degrees of freedom to allow spine stabilization system 100 to accommodate or avoid nerves, organs or other components of spine stabilization system 100. FIG. 6E depicts a view of one embodiment of connector body 50 showing tang 78 inferior to head 12 of transverse member 10. In this embodiment, when side plates 150A and 150B are biased in a first direction (such as indicated by arrows) and center plate 150C is biased in an opposite direction (such as indicated by an arrow), tang 78 may contact head 12 to impinge head 12 between tang 78 and side plates 150A and 150B. FIG. 6F depicts one embodiment of spine stabilization system 100 in which tang 78 is located superior to head 12. In this embodiment, when side plates 150A and 150B are biased in a first direction (e.g. into the paper) and center plate 150C is biased in an opposite direction (e.g. out of the paper), tang 78 may contact head 12 to impinge head 12 between tang 78 and side plates 150A and 150B.

Various instruments may be used in a minimally invasive procedure to form a spinal stabilization system in a patient. The instruments may include, but are not limited to, positioning needles, guide wires, dilators, bone awls, bone taps, sleeves, drivers, tissue wedges, rod length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, rods, closure members, transverse members, connectors, connector bodies, male threaded inserts, and plungers.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

A targeting needle may be used to locate an entry point in a vertebral body for a bone fastener of a bone fastener assembly. In some embodiments, the targeting needle may be a Jamshidi® bone marrow biopsy needle. In some embodiments, a targeting needle may include an outer housing and a member. In some embodiments, an outer housing may include a hollow shaft and a handle. In some embodiments, scale markings may be printed, etched, or otherwise placed on the hollow shaft. In some embodiments, one or more scale markings may be used to approximate a length of a bone fastener needed for a vertebra. In some embodiments, a handle may provide a grip that allows a user to manipulate the targeting needle. In some embodiments, a handle may include a female threaded portion. In some embodiments, the female threaded portion may couple to threading on a portion of a targeting needle member to secure the member to the outer housing.

In some embodiments, a guide wire may be used to advance components into the patient, create a tissue plane, or the like. In some embodiments, the guide wire may be an 18-gauge K-wire. In some embodiments, guide wires provided in an instrumentation set are about 46 cm in length. In some embodiments, the length of a guide wire may allow a surgeon and/or assistants to hold at least one portion of the guide wire at all times when the guide wire is inserted into vertebral bone, even during insertion, use, and removal of instruments along a length of the guide wire. A guide wire that can be held continuously during a surgical procedure may inhibit removal or advancement of the guide wire from a desired position during a minimally invasive surgical procedure.

Dilators may be used during a minimally invasive surgical procedure to push aside tissue and create space to access vertebral bone. Dilators in an instrumentation set may increase in diameter incrementally by a selected amount. For example, outside diameters of dilators in an instrumentation set may increase sequentially by increments of about 0.5 mm.

A guide wire positioned in vertebral bone may be held near a top of a dilator inserted over the guide wire at a surgical site.

A detachable member may be used as a guide to install components of spine stabilization system 100. A detachable member may be coupled to a bone fastener or coupled to a rod that is coupled to a bone fastener. A distal end of a detachable member may be tapered or angled to reduce bulk at a surgical site. Instruments may be inserted into the detachable member to manipulate components of spine stabilization system 100. Movement of the detachable member may alter an orientation of components relative to rod 5. In some embodiments, a detachable member may be used as a retractor during a spinal stabilization procedure.

A detachable member may include one or more channels in a wall of the detachable member to allow access to an adjacent vertebra. A channel in a wall of a detachable member may allow access to a vertebra that is to be stabilized with spinal stabilization system 100 being formed. In some embodiments, a single-channel detachable member may be coupled to connector body 50 to be coupled to first rod 5.

Instruments may access ipsilateral rod 5, contralateral rod 5, transverse members 10 and connector 60 through a passage in a detachable member. In some embodiments, a channel in a wall of a detachable member may extend a full length of the detachable member. In some embodiments, especially in embodiments of multi-channel detachable members, a channel in a wall of a detachable member may extend only a portion of the length of the detachable member. In some embodiments, a channel in a wall of a detachable member may extend 25%, 50%, 75%, 80%, 90%, 95% or more of the length of the detachable member. A channel may extend to a distal end of a detachable member.

A channel in a detachable member may be any of a variety of shapes. A channel may have a width that exceeds a width (e.g., a diameter) of rod 5 or transverse member 10 that is to be inserted in the channel. In some embodiments, a channel may be a linear opening parallel to a longitudinal axis of the detachable member. In some embodiments, a channel may have a non-linear shape including, but not limited to, a helical pattern, an arc, an "L" shape, or an "S" shape.

A cross section transverse to a longitudinal axis of a detachable member may have shapes including, but not limited to, circular, ovoid, square, pentagonal, hexagonal, and combinations thereof. In some embodiments, a detachable member may be hollow. In certain embodiments, a thickness of a hollow detachable member may be uniform. In certain embodiments, a thickness of a hollow detachable member may vary along the length of the detachable member. A detachable member with a passage extending longitudinally from a first end of the detachable member to a second end of the detachable member may be referred to as a "sleeve".

Detachable members may be of various lengths. Detachable members of different lengths may be used in the same surgical procedure. A detachable member length used in a spinal stabilization procedure may be determined by a patient's anatomy. Detachable members may be just short enough to allow manipulation by a medical practitioner above an incision in a patient. In some embodiments, detachable members may be about 3.5 to about 11.5 cm long. For example, a single-channel detachable member may be about 10 cm long. In some embodiments, detachable members may be about 11.5 cm to about 14 cm long. For example, a single-channel or a multi-channel detachable member may be about 12.5 cm long. A multi-channel detachable member may be longer than a single-channel detachable member. In some embodiments, a multi-channel detachable member may be at least about 15 cm long. For example, a multi-channel detachable member may be about 16 cm long. Detachable members that are too long may require a longer incision and/or a larger tissue plane for insertion of a spinal stabilization system. Insertion of rod 5 or transverse member 10 may be more difficult with detachable members that are longer than necessary. Detachable members with excess length may be bulky and hard to manipulate during a surgical procedure.

A detachable member may be flexible over its entire length or include a flexible portion near a proximal end of the detachable member. A flexible portion may allow positioning of a proximal portion of a detachable member in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

During surgery, first connector body 50 may be coupled to first spinal rod 5 and second connector body 50 may be coupled to second (i.e., contralateral) spinal rod 5. In some embodiments, a detachable member connected to first connector body 50 may be oriented towards second rod 5. In some embodiments, a detachable member coupled to first spinal rod 5 in a patient may be oriented towards second spinal rod 5 to reduce the required incision size. In some embodiments, a detachable member coupled to first spinal rod 5 in a patient may be oriented towards second spinal rod 5 to enable transverse member 10 to be advanced toward connector body 50 coupled to second spinal rod 5 in the patient. First transverse member 10 may be coupled to first connector body 50 and second connector body 50 may be coupled to second transverse member 10. First transverse member 10 may be rotated about head 12 of first transverse member 10. Rotation may include rotating first transverse member 10 about head 12 perpendicular to the central axis of passage 55, parallel to the central axis of passage 55, about a longitudinal axis of elongated section 14, or some combination thereof.

Figure 7A:
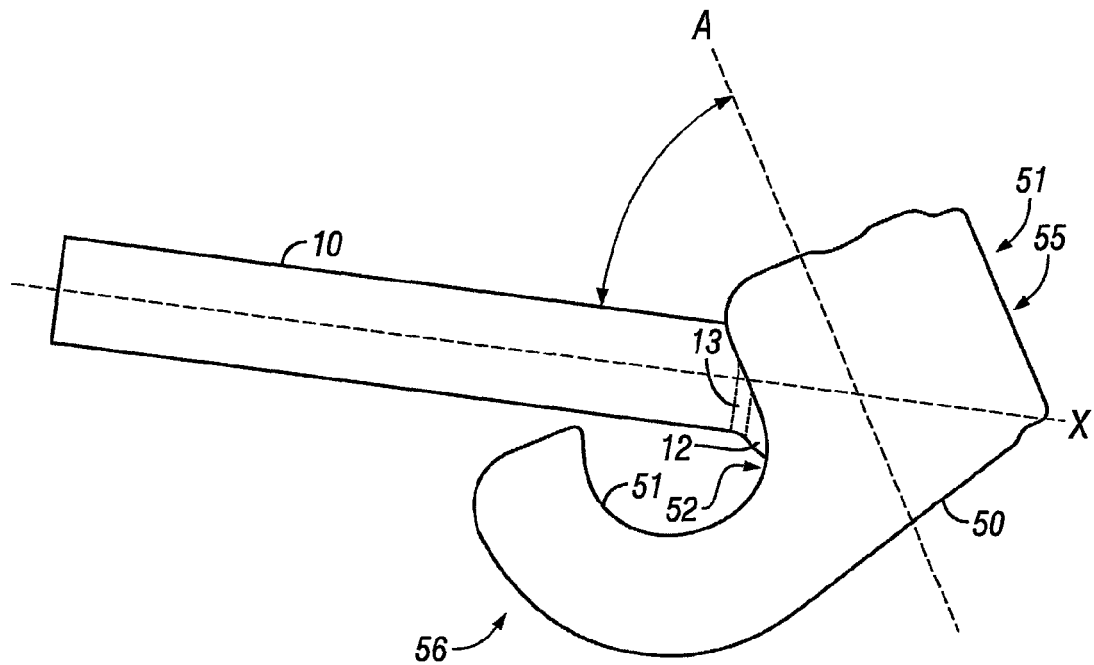
FIGS. 7A-7D depict views of a portion of one embodiment of a polyaxial transverse connector.

FIG. 7A depicts a view of one embodiment of connector body 50 having head 12 of transverse member 10 positioned therein. FIG. 7A also depicts axes A and X, with the intersection of axes A and X coinciding with head 12 of transverse member 10.

Figure 7B:
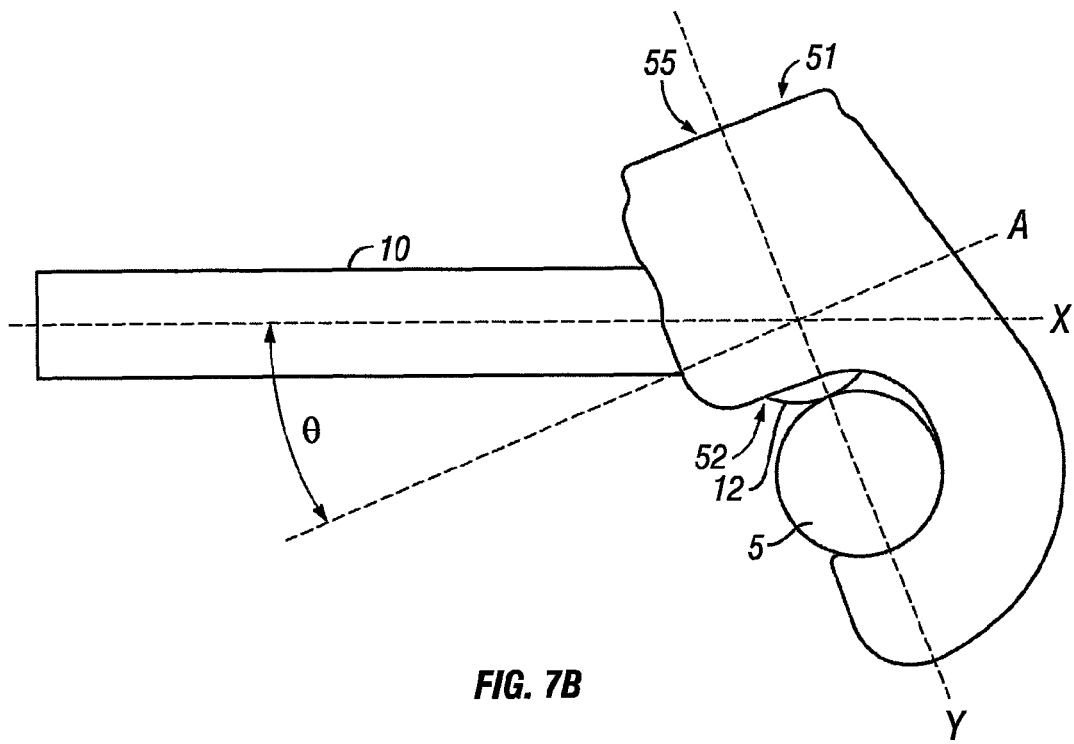

FIG. 7B depicts a view of one embodiment of connector body 50 positioned on rod 5 and having head 12 of transverse member 10 positioned therein. FIG. 7B further depicts axes A, X and Y, with the intersection of all three axes coinciding with head 12 of transverse member 10. FIG. 7B shows connector body 50 rotated about rod 5 past the point in which head 12 is directly above rod 5 (i.e., angle θ (Theta) between axes A and Y is not 90 degrees). By rotating connector body 50 about rod 5 to a selected position, the vertical height of transverse member 10 or spine stabilization system 100 may be optimized. For example, FIG. 7B depicts spine stabilization system 100 configured to have a lower profile.

Figure 7C:
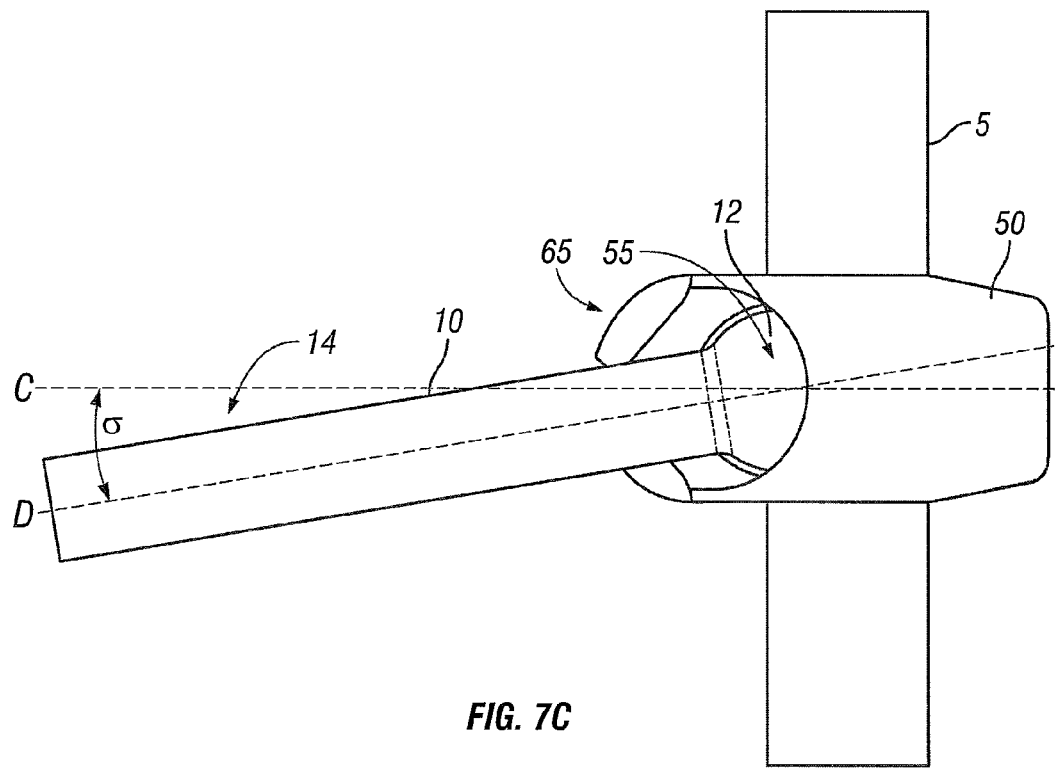

FIG. 7C depicts a view of a portion of one embodiment of spine stabilization system 100 with transverse member 10 able to rotate some angle σ (sigma) about head 12 positioned in connector body 50. FIG. 7C further depicts axes D of transverse member 10 at some angle σ (sigma) relative to axis C of connector body 50, with the intersection coinciding with head 12 of transverse member 10.

In some embodiments, by rotating connector body 50 about rod 5, the offset (such as offset 77 or 88) of spine stabilization system 100 may be selected. For example, if connector body 50 is rotated into the same horizontal plane as rod 5 (i.e., axis Y is aligned with axis X), there may be no offset. If connector body 50 is rotated into the vertical plane of rod 5 (i.e., head 12 is positioned directly above rod 5 such that axis Y is perpendicular to axis X and axis A is aligned with axis X), the offset (such as offset 77 or 88) of spine stabilization system 100 may be at a maximum.

Figure 7D:
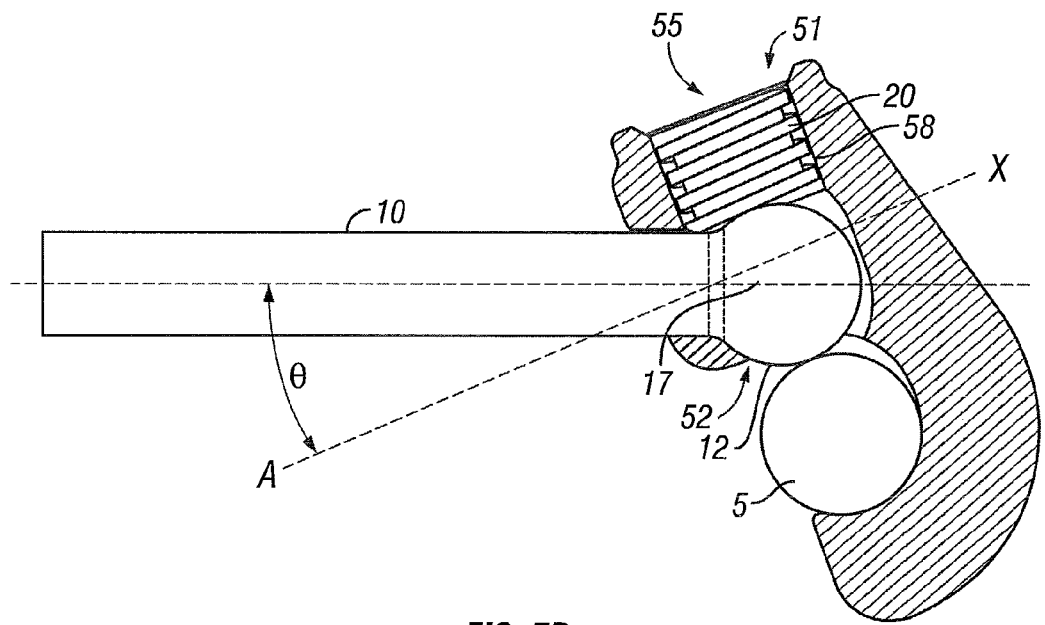

In some embodiments, head 12 may be positioned in cavity 54 or passage 55. Elongated sections 14 of first transverse member 10 and second transverse member 10 may be connected via connector 60. Male threaded insert 20 may be advanced into first connector body 50 to securely couple first connector body 50 to first transverse member 10 and rod 5. Male threaded insert 20 may be advanced into second connector body 50 to securely couple first connector body 50 to second transverse member 10 and rod 5. FIG. 7D depicts a view of one embodiment of connector body 50 connected to rod 5, with head 12 of transverse member 10 positioned in cavity 54 and male threaded insert 20 positioned in female threaded portion 58. With male threaded insert 20 impinging head 12 against rod 5, transverse member 10 may be inhibited from polyaxial motion such that a desired angle θ (theta) is maintained for spine stabilization system 100. Connector 60 may couple first transverse member 10 to second transverse member 10.

During a minimally invasive surgical procedure, a plane may be created in tissue from first connector body 50 to second connector body 50. Transverse members 10 may be positioned in the plane during the surgical procedure.

After transverse members 10 have been advanced into the patient and heads 12 of transverse members 10 has been positioned in first connector body 50 and second connector body 50, connector 60 may be advanced into the patient such that elongated sections 14 of transverse members 10 may be coupled together. In some embodiments, connector 60 may be connected to one elongated section 14 for advancement into the patient. In some embodiments, connector 60 may be advanced into the patient after both elongated sections 14 have been inserted and heads 12 have been positioned in connector bodies 50. In some embodiments, a tool may be used to advance connector 60 into the patient.

In some embodiments, after elongated sections 14 of transverse members 10 have been inserted in connector 60 and heads 12 have been positioned in cavities 54 such that spine stabilization system 100 is in a selected configuration with transverse members 10 oriented at a selected angle θ (theta), σ (sigma), or other rotation about head 12, male threaded inserts 20 may be inserted in connector body 50 to lock transverse members 10 in a selected orientation. In some embodiments, a driver may be used to advance male threaded inserts 20 in passages 55 of connector bodies 50.

In some embodiments, a detachable member may be held with a counter torque wrench. A counter torque wrench may inhibit transfer of force to the patient when male threaded inserts 20 are being secured in passages 55. Force may be applied to a counter torque wrench in a direction opposite to rotational force applied to a driver to prevent torque from damaging the spine, causing pain in the patient, or some other undesirable effect.

Minimally invasive procedures may involve locating a surgical site and a position for a single skin incision to access the surgical site. The incision may be located above and between vertebrae to be stabilized. An opening under the skin may be enlarged to exceed the size of the skin incision. Movement and/or stretching of the incision, bending of rod 5, and angulation of collars of bone fastener assemblies may allow the length of the incision and/or the area of a tissue plane to be minimized. In some embodiments, minimally invasive insertion of a spinal stabilization system may not be visualized.

In an embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bulls-eye" views are obtainable. Once the patient is positioned and the ability to obtain fluoroscopic images of the target levels for instrumentation has been confirmed, the patient may be prepared and draped sterilely.

Various techniques may be used to plan the skin incisions and entry points. An incision may be made in the skin. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200,000 epinephrine. Once the incision has been made, tissue surrounding the incision may be pulled and/or stretched to allow access to a target location in a vertebra.

A scalpel may be used to make a stab wound at a selected site. In an embodiment, the scalpel may be a #11 scalpel. A guide wire may be advanced into the patient. In some embodiments, the guide wire may be advanced to a bone fastener assembly coupled to first rod 5. In some embodiments, the guide wire may be advanced to first rod 5. Lateral fluoroscopic images may be obtained to indicate the position of guide wire 218. In some embodiments, the guide wire may be connected to rod 5.

Once the guide wire has been positioned near first rod 5, the guide wire may be used as a guide to position one or more successively sized dilators into the patient. A dilator may be a conduit with a regular shape (e.g., cylindrical) or an irregular shape (e.g., C-shaped). A dilator may form an opening through soft tissue. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact first rod 5. A distal end of a dilator may be tapered to facilitate positioning of the dilator proximate rod 5. An instrumentation set for spinal stabilization system 100 may include two, three, four, or more successively sized dilators. Lengths of dilators in a successively sized set may decrease with increasing diameter to facilitate removal of the smaller dilators.

After tissue dilation has been achieved, a large diameter dilator may be used to guide connector body 50, transverse member 10, male threaded insert 20, connector 60 and/or insertion instruments toward rods 5.

In some embodiments, connector body 50 may be assembled prior to surgery. Side plates 150A and 150B may be positioned on either side of center plate 150C. Protrusions 182A and 182B may be advanced into slots 190A and 190B. A pin may be inserted in openings 183A and 183B and slot 183C such that side plates 150A and 150B may move relative to plate 150C. In some embodiments, male threaded insert 20 may be inserted (via opening 51 formed by inner surfaces 151A and 151B and opening 155) in passage 55 formed by female threaded portions 158A and 158B along with opening 155.

In some embodiments, connector body 50 may be advanced into the patient and coupled to rod 5 before head 12 of transverse member 10 is positioned in connector body 50. Connector body 50 may be advanced into the patient and positioned such that rod 5 is seated in rod hook 56. In some embodiments, once rod 5 is seated in rod hook 56, other components of spine stabilization system 100 may be coupled to connector body 50. In some embodiments, one or more components of spine stabilization system 100 may be coupled to connector body 50 prior to insertion of connector body 50. For example, in some embodiments, head 12 of transverse member 10 may be positioned in connector body 50, plunger 70 may be positioned in connector body 50, and/or male threaded insert 20 may be advanced into connector body 50 prior to insertion of connector body 50 into the patient.

In some embodiments, a tool may be used to couple connector body 50 to rod 5. The tool may attach to first end 50A of connector body 50. The tool may be flexible or hinged to allow a surgeon to rotate or manipulate connector body 50 in the patient.

In some embodiments, transverse member 10 may be advanced into the patient. In some embodiments, transverse member 10 may be advanced down a sleeve connected to first connector body 50 located on first rod 5. In some embodiments, advancement of transverse member 10 down the sleeve may involve advancing head 12 leading elongated section 14. Head 12 may be positioned in cavity 54 and transverse member 10 may be rotated about head 12 to position transverse member 10 in a selected orientation. In some embodiments, transverse member 10 may be advanced down a sleeve connected to second connector body 50 located on second rod 5. Transverse member 10 may be advanced down the sleeve and across the spine such that transverse member 10 is in a selected orientation before head 12 is positioned in connector body 50.

In some embodiments, connector body 50 may be coupled to rod 5 after head 12 of transverse member 10 is positioned in connector body 50. Head 12 of transverse member 10 may be positioned in connector body 50 such that transverse member 10 can rotate about one or more axes. In some embodiments, head 12 of transverse member 10 may be inserted directly into cavity 54 in connector body 50. In some embodiments, positioning of head 12 in cavity 54 may require head 12 to pass through other features of connector body 50. In some embodiments, cavity 54 may form a portion of passage 55, such that head 12 may be advanced through passage 55 into cavity 54. In some embodiments, head 12 may be advanced in cavity 54 via opening 51 at first end 50A. In some embodiments, head 12 maybe inserted through opening 52 at second end 50C and positioned in cavity 54. In some embodiments, such as the embodiment depicted in FIGS. 6A-6F, head 12 of transverse member 10 may be positioned in cavity 54 when side plates 150A and 150B are in a first position relative to center plate 150C.

In some embodiments, head 12 may have keyed surfaces 17 such that head 12 may be advanced into (or removed from) passage 55 or cavity 54 in a first orientation and rotated into a second orientation such that removal is inhibited. Once head 12 is positioned in cavity 54, the polyaxial nature of transverse member 10 may allow a surgeon to rotate transverse member 10 into a desired orientation. A desired orientation may include orienting a bend or offset 15 in transverse member 10 to avoid the dural space, a spinous process, or some other organ or anatomical landmark in the patient.

Connector 60 may couple transverse members 10 together to couple rods 5 and form spine stabilization system 100. In some embodiments, connector 60 may be coupled to one or both transverse members 10 prior to insertion of connector 60. In some embodiments, connector 60 may be positioned in the patient and transverse members 10 may be advanced into the patient and elongated sections 14 may be inserted into connector 60. Connector 60 may securely couple to transverse members 10 to inhibit withdrawal of elongated sections 14 from connector.

In some embodiments, plunger 70 may be positioned in connector body 50 to provide a desired offset 77 in spine stabilization system 100. In some embodiments, plunger 70 may be positioned between male threaded insert 20 and head 12 of transverse member in cavity 54. In some embodiments, plunger 70 may be positioned below head 12 of transverse member in cavity 54. In some embodiments, plunger 70 may be positioned in connector body 50 prior to insertion of connector body 50 into a patient.

In some embodiments, once elongated sections 14 of transverse members 10 have been securely coupled via connector 60, male threaded inserts 20 may be advanced into connector bodies 50 to securely couple transverse members 10 to connector bodies 50. In some embodiments, a tool may be inserted through a sleeve or dilator such that an end engages tool portions 22 on male threaded insert 20. Male threaded insert 20 may be advanced into connector body 50. In some embodiments, advancement of male threaded member 20 in connector body 50 causes end 25 to protrude through opening 52 and impinge rod 5 against rod hook 56. In some embodiments, advancement of male threaded member 20 in connector body 50 causes end 25 to contact plunger 70 such that plunger 70 protrudes through opening 52 and impinges rod 5 against rod hook 56. In some embodiments, the rotation of male threaded insert 20 in passage 55 may bias side plates 150A and 150B in a first direction or may bias center plate 150C in an opposite direction. In some embodiments, biasing side plates 150A and 150B in a first direction or biasing center plate 150C in an opposite direction may impinge rod 5 between rod hook 56 and center plate 150C. In some embodiments, surfaces 157A and 157B may provide additional support for connector body 50.

In some embodiments, once spine stabilization system 100 has been assembled, adjustments may be made to various components. In some embodiments, adjustments may be made for patient comfort, for a desired rigidity, or some other medical result.

Torque required to advance male threaded insert 20 in connector body 50 or seat male threaded insert 20 or plunger 70 against rod 5 may be a source of pain and/or injury to a patient. In some embodiments, a sleeve may be held with a counter torque wrench as male threaded insert 20 is advanced into female threaded portion 58.

In some embodiments, a counter torque wrench sleeve may be inserted through the opening in the body over a sleeve. The counter torque wrench sleeve may be advanced toward the spine until rod 5 is seated in the counter torque wrench sleeve. Force may be applied to the counter torque wrench in a direction opposite to any rotational force applied to a driver used to advance male threaded insert 20. After male threaded insert 20 is successfully secured in passage 55, the driver may be removed from the sleeve. One or more sleeves may be uncoupled from rods 5. The sleeves may be withdrawn from the patient and the incision may be closed.

In some embodiments, a spinal stabilization system may be inserted using an invasive procedure. Since insertion of a spinal stabilization system in an invasive procedure may be visualized, cannulated components (e.g., bone fasteners) and/or instruments (e.g., detachable members) may not be needed for the invasive (i.e., open) procedure. Thus, connector body 50, transverse member 10, connector 60, or male threaded insert 20 used in an invasive procedure may differ from components used in a minimally invasive procedure.

In some embodiments, tools used in an invasive procedure may be similar to tools used in a minimally invasive procedure. In certain embodiments, methods of installing spinal stabilization system 100 in an invasive procedure may be similar to methods of installing spinal stabilization system 100 in a minimally invasive procedure.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A transverse connector assembly, comprising;
a connector body having a first end, a mid portion, and a second end, wherein the first end has a female threaded opening, wherein the second end has a rod hook, wherein the mid portion has a cutout and a cavity, and wherein the female threaded opening of the first end and the cutout and the cavity of the mid portion form a passage having a central axis;
a male threaded insert for releasably coupling to the connector body via the female threaded opening of the first end of the connector body; and
a transverse member having a head portion and an arm portion, wherein the arm portion has at least one curvature, wherein the head portion of the transverse member comprises a flattened area,
wherein the head portion of the transverse member is insertable into the passage of the connector body such that the head portion of the transverse member is positioned in the cavity, wherein the arm portion extends from the head portion of the transverse member through the cutout of the mid portion of the connector body, and wherein the head portion of the transverse member rotates within the cavity of the mid portion of the connector body, wherein the arm portion of the transverse member is movable longitudinally with respect to the central axis of the passage of the connector body.

2. The transverse connector assembly of claim 1, wherein the arm portion of the transverse member comprises a second curvature.

3. The transverse connector assembly of claim 2, wherein the first curvature and the second curvature form an offset.

4. The transverse connector assembly of claim 3, wherein the offset avoids contact with a portion of a spine.

5. The transverse connector assembly of claim 1, wherein the head portion of the transverse member comprises an area with an associated curvature different than the curvature of the head portion.

6. The transverse connector assembly of claim 1, further comprising:
a plunger for positioning in the passage proximal to the head of the transverse member.

7. A transverse connector system, comprising;
a first connector body having a first end, a mid portion, and a second end, wherein the first end has a female threaded opening, wherein the second end has a rod hook, wherein the mid portion has a cutout and a cavity, and wherein the female threaded opening of the first end and the cutout and the cavity of the mid portion form a passage having a central axis;
a second connector body having a first end, a mid portion, and a second end, wherein the first end has a female threaded opening, wherein the second end has a rod hook, wherein the mid portion has a cutout and a cavity, and wherein the female threaded opening of the first end and the cutout and the cavity of the mid portion form a passage having a central axis;
a first male threaded insert for releasably coupling to the first connector body via the female threaded opening of the first end of the first connector body;
a second male threaded insert for releasably coupling to the second connector body via the female threaded opening of the first end of the second connector body;
a first transverse member having a head portion and an arm portion, wherein the arm portion of the first transverse member has at least one curvature, wherein the head portion of the first transverse member is insertable into the passage of the first connector body such that the head portion of the transverse member is positioned in the cavity, wherein the arm portion extends from the head portion of the first transverse member through the cutout of the mid portion of the first connector body, and wherein the head portion of the first transverse member rotates within the cavity of the mid portion of the connector body, wherein the arm portion of the first transverse member is movable longitudinally with respect to the central axis of the passage of the first connector body;
a second transverse member having a head portion and an arm portion, wherein the arm portion of the second transverse member has at least one curvature, wherein the head portion of the second transverse member is insertable into the passage of the second connector body such that the head portion of the transverse member is positioned in the cavity, wherein the arm portion extends from the head portion of the second transverse member through the cutout of the mid portion of the second connector body, and wherein the head portion of the second transverse member rotates within the cavity of the mid portion of the connector body, wherein the arm portion of the second transverse member is movable longitudinally with respect to the central axis of the passage of the second connector body; and
a connector for coupling the arm portion of the first transverse member and the arm portion of the second transverse member.

8. The transverse connector system of claim 7, wherein the arm portion of the first or second transverse member comprises a second curvature.

9. The transverse connector system of claim 8, wherein the first curvature and the selected curvature form an offset.

10. The transverse connector system of claim 9, wherein the offset avoids contact with a portion of a spine.

11. The transverse connector system of claim 7, wherein the head of the first or second transverse member comprises a flattened area.

12. The transverse connector system of claim 7, wherein the head of the first transverse member comprises an area having a curvature different from the curvature of the head.

13. The transverse connector system of claim 7, further comprising:
a plunger for positioning between one or more of the head of the first transverse member and the first rod and the second transverse member and the second rod, wherein the plunger forms a second offset in the transverse polyaxial connector.

* * * * *